(12) United States Patent
Paufique

(10) Patent No.: US 11,986,552 B2
(45) Date of Patent: May 21, 2024

(54) **HYDROLYSATE OF *PICHIA MINUTA* AND COSMETIC USE THEREOF FOR CONTROLLING HAIR LOSS AND STIMULATING REGROWTH**

(71) Applicant: SOCIETE LIMOUSINE D'APPLICATION BIOLOGIQUE (SILAB), Objat (FR)

(72) Inventor: Jean Paufique, Objat (FR)

(73) Assignee: Societe Limousine D'Application Biologique (SILAB), Objat (FR)

( * ) Notice: Subject to any disclaimer, the term of this patent is extended or adjusted under 35 U.S.C. 154(b) by 0 days.

(21) Appl. No.: 18/298,567

(22) Filed: Apr. 11, 2023

(65) Prior Publication Data

US 2023/0240976 A1   Aug. 3, 2023

Related U.S. Application Data

(62) Division of application No. 16/476,428, filed as application No. PCT/EP2018/050462 on Jan. 9, 2018, now abandoned.

(30) Foreign Application Priority Data

Jan. 9, 2017   (FR) .................................... 17 70024

(51) Int. Cl.
 *A61K 8/99* (2017.01)
 *A61K 8/64* (2006.01)
 *A61Q 7/00* (2006.01)
(52) U.S. Cl.
 CPC .................. *A61K 8/99* (2013.01); *A61K 8/64* (2013.01); *A61Q 7/00* (2013.01)

(58) Field of Classification Search
 None
 See application file for complete search history.

(56) References Cited

U.S. PATENT DOCUMENTS

| 3,713,979 | A | 1/1973 | Slodki et al. |
| 2002/0011186 | A1 | 1/2002 | Tanaka et al. |
| 2003/0134781 | A1 | 7/2003 | Carmichael et al. |
| 2005/0142095 | A1 | 6/2005 | Scancarella et al. |
| 2006/0148039 | A1 | 7/2006 | Kobayashi et al. |
| 2013/0287715 | A1* | 10/2013 | Justen .................... A61P 17/06 424/59 |

FOREIGN PATENT DOCUMENTS

| FR | 2938768 A1 | 5/2010 |
| FR | 3016521 A1 | 7/2015 |
| WO | 2011103624 A1 | 9/2011 |

OTHER PUBLICATIONS

International Search Report from PCT application No. PCT/EP2018/050462, dated Apr. 19, 2018.
Annette Herscovics, Structure and Function of Class I œ 1,2-mannosidases involved in glycoprotein synthesis and endoplasmic reticulum quality control, Biochimie 83 (2001), 757-762.

\* cited by examiner

*Primary Examiner* — Susan Hoffman
(74) *Attorney, Agent, or Firm* — Greer, Burns & Crain, Ltd.

(57) ABSTRACT

A cosmetic active principle including a hydrolysate of *Pichia minuta* comprising at least peptides. Additionally, the use of the cosmetic active principle including a hydrolysate of *Pichia minuta* comprising at least peptides for controlling hair loss and stimulating regrowth. Also, compositions containing same and a cosmetic hair treatment method.

15 Claims, 3 Drawing Sheets

Figure 1:
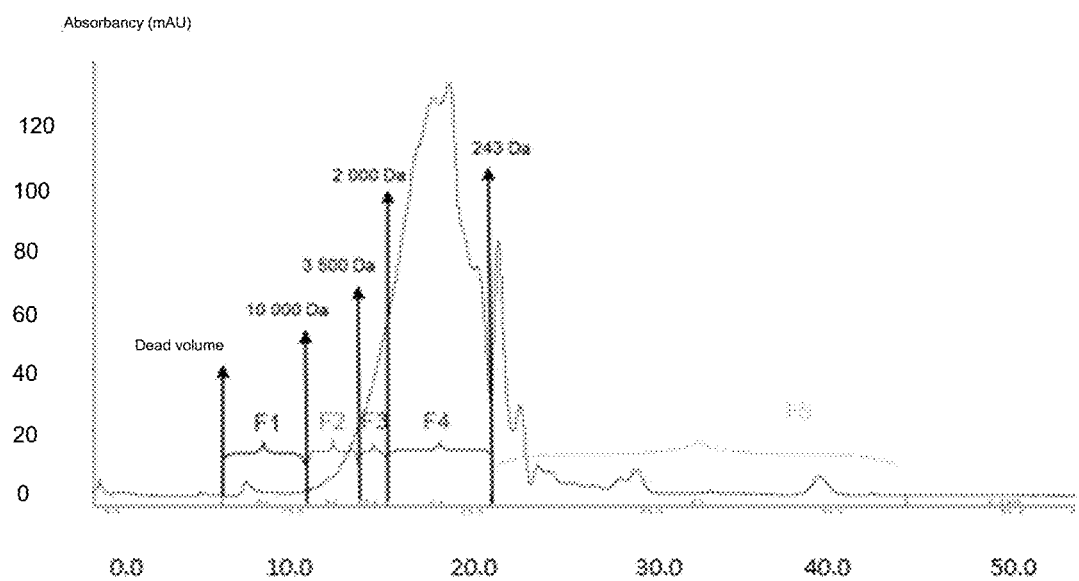

HYDROLYSATE OF *PICHIA MINUTA* AND COSMETIC USE THEREOF FOR CONTROLLING HAIR LOSS AND STIMULATING REGROWTH

RELATED APPLICATIONS

This application is a divisional of U.S. patent application Ser. No. 16/476,428, filed on Jul. 8, 2019, now abandoned which is a national phase application of International Application No. PCT/EP2018/050462 filed on Jan. 9, 2018 which claims priority to French Application No. 1,770,024 filed on Jan. 9, 2017, the entity of all of which are incorporated herein by reference.

BACKGROUND

This invention relates to a particular cosmetic active ingredient obtained by yeast hydrolysis and its use for fighting hair loss and promoting regrowth.

In a society that places importance on appearance, hair is a symbol of beauty and strength whose condition has a significant impact on one's self-esteem and image. The acceleration of hair loss, scientifically known as alopecia, is perceived as a sign of early aging and can dramatically affect the quality of life of those affected.

This is why many cosmetic products aimed at slowing hair loss have been proposed, with a significant increase over the last ten years.

Alopecia is a common disorder with its androgenetic form being the most common. It affects up to 30% of men under 30 and more than 50% of men over age 50. This progressive disorder, which is not a disease (Prie B. et al., "Oxidative stress in androgenetic alopecia", Journal of Medicine and Life Vol. 9, Issue 1, January-March 2016, pp. 79-83), is characterized by the appearance of finer, shorter and non-pigmented hair which turns to vellus hair. It is caused by two main factors, genetic and hormonal, which cause hypersensitivity to a hormone: dihydrotestosterone (DHT). The latter is responsible for all biological changes associated with this disorder. In addition, certain environmental parameters may also promote the appearance of androgenetic alopecia (AGA). This is the case with repeated use of aggressive hair products (dyes and other chemical agents), smoking or UV exposure.

Retention of thick hair is the result of equilibrium between hair loss and regrowth. Losing hair is a natural phenomenon, with an individual losing between 50 and 125 every day. Thanks to a process of regeneration, a constant renewal thereof is ensured: the so-called life cycle of the hair or hair growth cycle. It is divided into three phases:
- anagen (growth);
- catagen (degeneration);
- telogen (latency).

The hair or hair follicle consists of two main elements. The dermal papilla is the driving force of its growth and lies at the base of the follicle. It is composed of fibroblasts able to emit growth signals. These are then captured by the cells of the hair matrix. This structure that surrounds the papilla is home to keratinocytes. In response to these signals, they will proliferate to trigger the formation of a new hair stalk.

Hair growth is an energy-consuming process that requires functional mitochondria in the cells, the morphological state of these dynamic organelles conditioning energy production.

Other regulatory factors play a major role in the regeneration of hair and exhibit a malfunction during androgenetic alopecia:

- the "signal" molecules, which allow the cells to communicate with each other; within hair follicles, they orchestrate the action of the fibroblasts of the papilla and keratinocytes of the matrix to ensure hair growth;
- epigenetics.

Currently, two chemical molecules are used in the treatment of androgenetic alopecia: minoxidil and finasteride. However, they are effective in less than 50% of cases and have significant side effects (oily hair, dandruff, skin irritation, libido problems). There is therefore a real need for a new approach to promote hair growth while avoiding the aforementioned problems.

In response, the invention proposes a natural cosmetic active ingredient, derived from yeast, able to act on three mechanisms for regulation of the regrowth of hair.

Several hydrolysates of yeast have already been used in cosmetics, such as hydrolysates of *Saccharomyces cerevisiae, Pichia anomala* or *Torulaspora delbrueckii*. However, the invention relates to a hydrolysate obtained from a different yeast, *Pichia minuta*, which is very different from already known yeasts used in cosmetics and which exhibits its own characteristics.

BRIEF SUMMARY

In particular, the invention relates to a cosmetic active ingredient including a hydrolysate of *Pichia minuta*, in particular a hydrolysate of *Pichia minuta* at least comprising peptides.

Advantageously, such an active ingredient is able to both stimulate mitochondrial dynamics for hair growth and correct expression defects affecting the "signal" and epigenetic molecules associated with androgenetic alopecia. The cosmetic active ingredient of the invention thus makes it possible to reactivate the dermal papilla and stimulate growth of hair follicles.

As a consequence, the invention also relates to the non-therapeutic cosmetic use of such an active ingredient when applied to hair and/or scalp, for fighting hair loss and enable regrowth.

The invention also relates to cosmetic compositions, containing at least 0.05% by weight, of the active ingredient of the invention, as well as a non-therapeutic cosmetic method for fighting hair loss and activating its regrowth by application of such compositions to the hair or scalp.

DETAILED DESCRIPTION OF THE DRAWINGS

Figure 2:
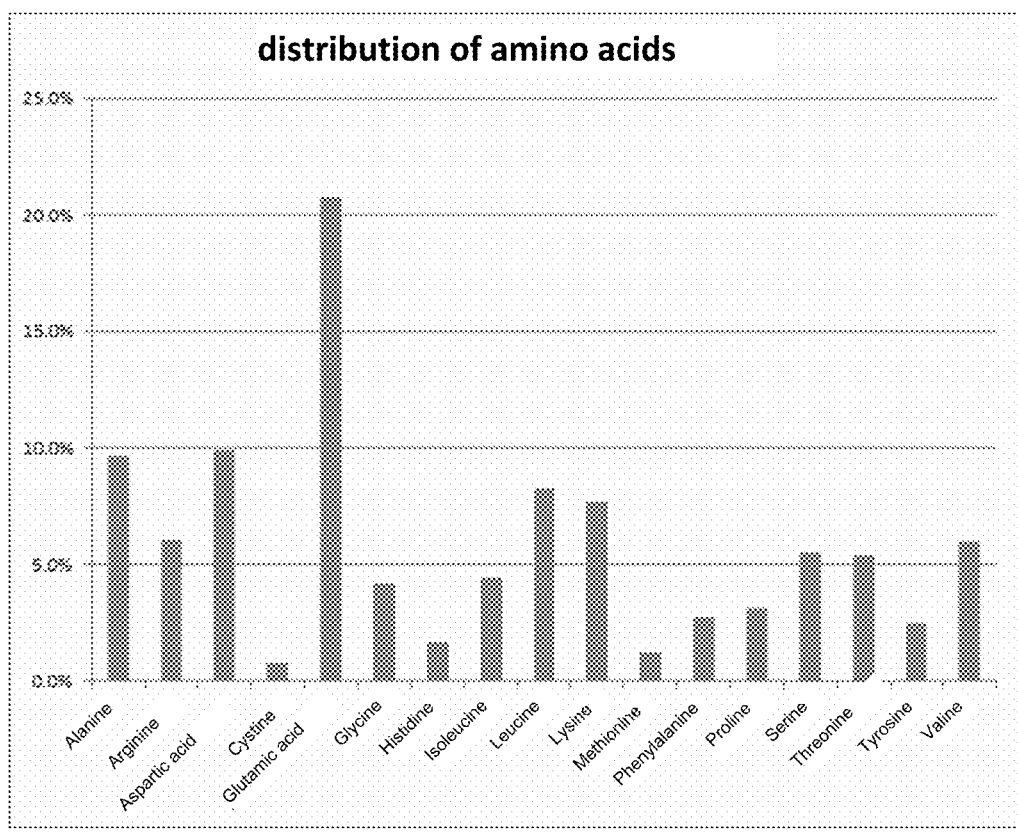
Figure 3:
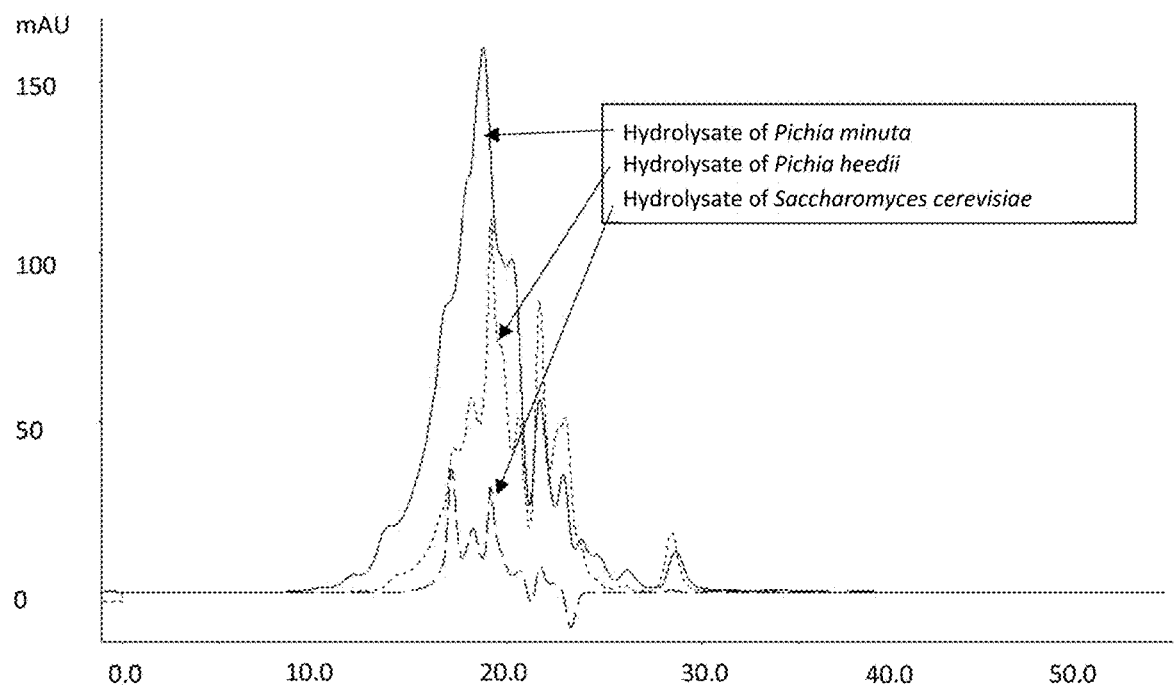

Other features and advantages will become apparent from the detailed description of the invention which follows, in which:

FIG. 1 represents the chromatographic profile (HPLC/RI) of the hydrolysate peptides of example 1, FIG. 2 represents the aminogram of the peptides of the active ingredient of the invention of example 1, FIG. 3 represents the chromatogram of the proteins of the three products presented in the Comparative Test 1, obtained using the same process starting for 3 different yeasts: *Pichia minuta, Pichia heedii* and *Saccharomyces cerevisiae,*

Figure 4A:
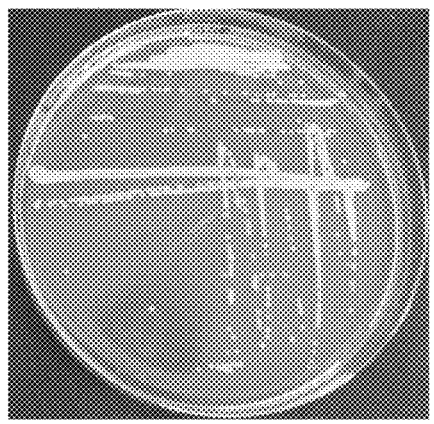
Figure 4B:
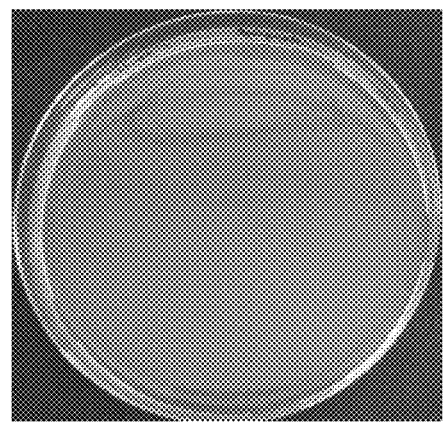
Figure 5A:
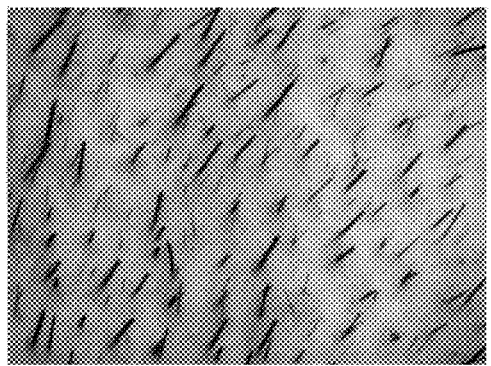
Figure 5B:
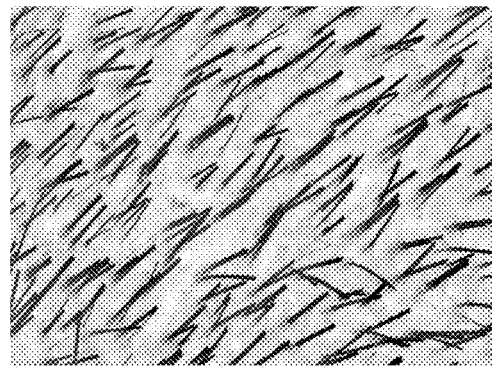
Figure 6A:
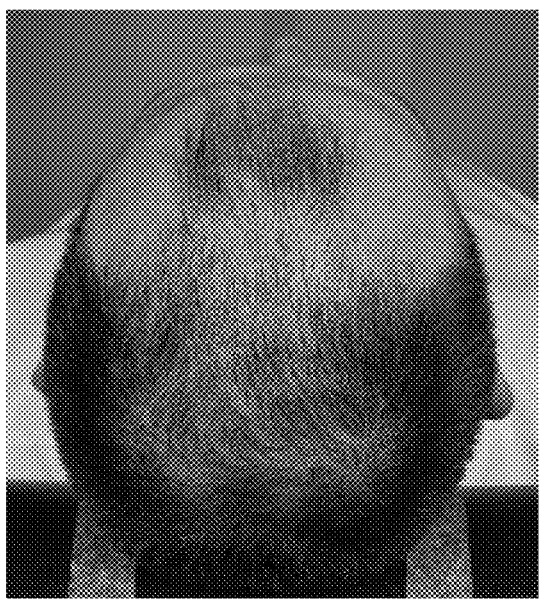
Figure 6B:
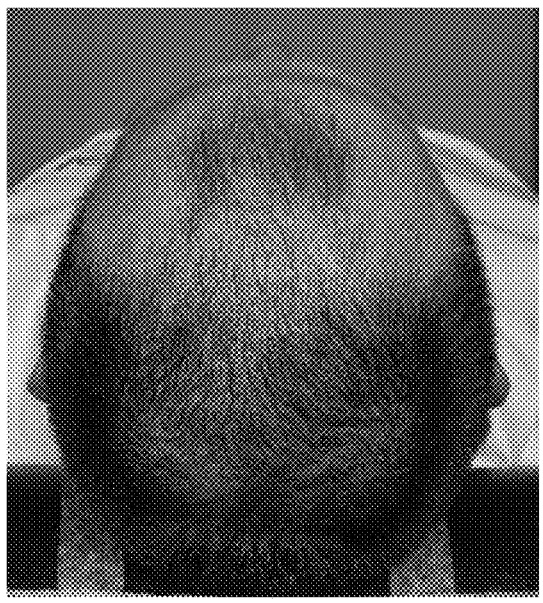

FIG. 4A represents an agar culture medium on which a biomass of *Pichia minuta* was inoculated and incubated for 48 h at 30° C., FIG. 4B represents an agar culture medium on which a hydrolysate of *Pichia minuta* was inoculated and incubated for 48 h at 30° C., FIG. 5A represents an enlarged photo of the scalp before application of a composition of the invention, FIG. 5B shows a zoomed in picture of a scalp after 8 months of application of a composition of the invention (point II.1), FIG. 6A represents a photo of a scalp before application of a composition of the invention, and, FIG. 6B shows a picture of a scalp after 8 months of application of a composition of the invention (point II.1)

DEFINITIONS

For the purposes of the invention, the term "cosmetic active agent" or "cosmetic active ingredient" means at least one molecule, preferentially a set of molecules having an effect on the cells of the hair and/or the scalp, in particular on the fibroblasts of the dermal papilla and the cells of the hair matrix.

For the purposes of the invention, the terms "protein fraction" or "peptide compounds" of the hydrolysate of *Pichia minuta* means all proteins and peptides present in the hydrolysate of *Pichia minuta*.

For the purposes of the invention, the term "hydrolysate of *Pichia minuta*" means any active ingredient derived from *Pichia minuta* yeast, obtained by a process comprising at least one step of enzymatic or chemical hydrolysis of *Pichia minuta*. The term hydrolysate of *Pichia minuta* excludes molecules produced solely by fermentation of *Pichia minuta*.

"*Pichia minuta*", within the meaning of the invention, means any yeast of the Saccharomycetaceae family, of the *Ogataea* genus and *Pichia minuta* species. The *Pichia minuta* yeast has been registered in several yeast collections, under numbers ATCC 26176, CBS 6511, MUCL 27758, MUCL 29976, DSM-70275, NRRL Y-411, NRRL Y-7953, NRRL Y-10948, Y-172, Y-2081, Y-2516, NCYC-499, 3622T, 9442, 3615T, NBRC 1473, NBRC 0975T, NBRC 10402, NBRC 10746. It is also known by other names: *Candida methanolovescens, Ogataea* minuta, *Ogataea nonfermentans. Pichia minuta* can be isolated from the azalea flower, *Rhododendron* indicum.

For the purposes of the invention, the term "atomization carrier" is understood to mean a neutral adjuvant added to a solution in order to produce a powder during spray drying.

DETAILED DESCRIPTION OF THE INVENTION

The invention therefore relates to a cosmetic active ingredient including a hydrolysate of *Pichia minuta*.

The hydrolysate of *Pichia minuta* at least contains peptides. Preferably, the hydrolysate of *Pichia minuta* contains peptides which have a molecular weight of less than 3500 Da, preferably between 243 and 3500 Da. These peptides play an important role in the effectiveness of the active ingredient of the invention.

Preferably, the peptides which have a molecular weight of less than 3500 Da represent at least 50% by weight of the protein fraction of the hydrolysate, still more preferably at least 80%.

In the hydrolysate, the protein fraction represents at least 40% by weight of the hydrolysate dry matter, preferably between 40 and 90%, more preferably between 50 and 70%.

The peptide compound content is preferentially determined by the LOWRY method (Lowry et al., Protein measurement with the folin reagent, J. Biol. Chem., 193, 265, 1951).

The amino acids which make up more than 5%, constituting the peptides of the hydrolysate (percent relative to the whole of the amino acids present in number) are preferably: alanine, arginine, aspartic acid, glutamic acid, leucine, lysine, serine, threonine, valine.

The aminogram of the peptides which make up the hydrolysate of the invention can be obtained by ion exchange chromatography after acid hydrolysis of the sample.

The hydrolysate also preferably comprises sugars and/or minerals.

Preferably, the sugars represent at least 5% by weight of hydrolysate dry matter, in particular between 5 and 25%, more preferably between 10 and 20%.

The sugar content of the hydrolysate can be determined by the DUBOIS method (Dubois M et al., Analytical Chemistry, 28, 3, 350-356, 1956).

The minerals present in the hydrolysate are preferably calcium, potassium, sodium, chlorine and phosphorus. The analysis of the minerals constituting the ashes of the hydrolysate was carried out by optical emission spectrometry (ICP/OES) and the measurement of chloride ions by titration with silver nitrate.

Preferably, the ash content is between 5 and 35% by weight of hydrolysate dry matter, more preferably between 20 and 30%.

The crude ash content can be determined by weighing the residues resulting from the incineration of the samples of the active ingredient of the invention at 550° C., in an electric muffle furnace.

The hydrolysate of the invention can be obtained by chemical (acid or base) or enzymatic hydrolysis. Preferably, an enzymatic hydrolysate is used.

The active ingredient of the invention can be in solid or liquid form.

When it is in liquid form, the active ingredient of the invention is preferably the hydrolysate as described above. It is in the form of a clear liquid, with a weak odor and a slightly orangish yellow color.

When it is in solid form, the active ingredient of the invention is preferably made up of the hydrolysate of *Pichia minuta* as previously described and of a carrier chosen from maltodextrin, gum arabic, soy lecithin or isomalt. According to one particularly suitable production, the hydrolysate represents between 25 and 75% of the weight of the active ingredient, preferably between 40 and 60%.

In the case of a solid form in which the active ingredient is associated with a carrier, the protein, sugar and ash contents in the active ingredient are modified, the carrier generally comprising mainly of sugars. In the case where the atomization carrier is maltodextrin, in an amount between 25 and 75%, preferably between 40 and 60%:

the peptides represent at least 12%, in particular between 12 and 53% by weight of dry matter of the active ingredient, preferably between 20 and 42%, the sugars represent between 32 and 80% by weight of dry matter of the active ingredient, preferably between 46 and 68%, the ashes represent between 5 and 23% by weight of dry matter of the active ingredient, preferably between 8 and 18%.

The hydrolysate constituting the active ingredient of the invention can be obtained by any process comprising at least one step of hydrolysis of *Pichia minuta*, in particular a step for hydrolysis of the proteins. Preferably, it is obtained by a process involving a step of enzymatic hydrolysis, in particular of enzymatic hydrolysis of the proteins, that is to say a hydrolysis carried out enzymatically by means of proteolytic enzymes. This may be, for example, proteases of plant origin or derived from microorganisms.

Prior to the process for obtaining the hydrolysate as such, the biomass of *Pichia minuta* should be produced. This step is carried out according to the culture method of the yeasts in a medium appropriate for their development, in a manner conventional to those skilled in the art.

Once the biomass has been obtained, hydrolysis is carried out in order to obtain active molecules. According to a particularly suitable embodiment, the active ingredient is obtained by the implementation of the following steps:

solubilization of the biomass of *Pichia minuta* in water hydrolysis of proteins: hydrolysis conditions are chosen to hydrolyze both the walls of the yeasts and the intracellular environment of the yeasts to promote bioactive peptide enrichment; preferably the hydrolysis is carried out enzymatically by means of proteolytic enzymes, preferably-of plant origin or derived from microorganisms;

inactivation of the enzyme(s), preferentially by heat treatment: this inactivation is carried out according to the technical recommendation of the supplier(s) of the enzyme(s);

separation of the soluble and insoluble phases, preferably by centrifugation, and recovery of the soluble phase containing, among other things, peptides and soluble proteins, filtration to remove still suspended particles, Purification by filtration to remove high molecular weight molecules (enzymes and polymers . . . ), preferably molecules of molecular weight greater than 5000 Da, obtaining a filtrate, the hydrolysate of *Pichia minuta*, which constitutes a first form of the active ingredient of the invention, which is in liquid form.

The hydrolysate obtained at this stage may be further concentrated and/or purified in order to select the fractions of low molecular weight, preferably less than 3500 kDa, or even possibly less than 2000 kDa, by successive ultrafiltration steps through varying porosity filters, retaining the filtrates at each stage and/or by means of a chromatographic type method, for example to specifically enrich the hydrolysate in these molecules.

The hydrolysate can then be dried and combined with a carrier to be in solid form. This phase can be achieved by implementing the following steps:

an atomization carrier, preferably maltodextrin, is added to the hydrolysate of *Pichia minuta*, between 25 and 75% (mass/volume);

this solution is then concentrated under vacuum;

removal of bacteria is carried out by heat treatment;

atomization makes it possible to obtain a powder.

This presentation of the peptide hydrolysate corresponds to a highly concentrated form of active molecules, in particular, peptides.

The steps of the methods described above, taken individually, are common in the field of extractions of active ingredients from natural raw materials and a person skilled in the art is able to adjust the reaction parameters based on their general knowledge.

The active ingredient of the invention is particularly effective against hair loss and to activate its regrowth. In particular, the hydrolysate of *Pichia minuta* of the invention, when applied to the hair and/or scalp:

promotes mitochondrial dynamics, a key element for hair growth, corrects the expression modifications of the "signal" molecules appearing during androgenetic alopecia, controls epigenetic actors during androgenetic alopecia, and maintains dermal papilla activation and hair follicle growth during androgenetic alopecia.

The growth of hair follicles is a process requiring a high energy input. Within the cell, it is the mitochondria that ensure energy production. For this, these organelles are able to adapt their morphology and, ultimately, their activity: mitochondrial dynamics. This is based on two phenomena: fission and fusion. Fission is defined by the separation of mitochondria which are then smaller and produce less energy. Conversely, fusion corresponds to the grouping of mitochondria in the form of a network. This relies notably on the intervention of mitofusin 1 (MFN1), a membrane protein involved in the fusion of the outer mitochondrial membranes. This process allows them to intensify their metabolism and produce more energy in the form of ATP.

Mitochondrial dynamics is involved in the biology of hair follicles. In particular, it is known that the morphology of mitochondria evolves towards a fused form in dermal papilla cells. This phenomenon is accompanied by an increase in mitochondrial enzymatic activity and the production of ATP. These mitochondrial changes provide the energy required to pass or maintain the growth phase of the hair cycle (Mifude et al. "PDGF-AA-induced filamentous mitochondria benefit dermal papilla cells in cellular migration". International Journal of Cosmetic Science, 37, 266-271 (2015)).

Advantageously, the active ingredient of the invention is able to stimulate the synthesis of mitofusin 1 in the fibroblasts of the dermal papilla and thus to promote the growth of hair follicles.

In addition, the "signal" molecules present in the microenvironment of the dermal papilla are essential for hair growth. Three of them are deregulated in androgenetic alopecia:

IL-6 (Interleukin 6), which blocks the proliferation of the cells of the matrix and inhibits the growth of the hair shaft;

DKK1 (Dickkopf 1), an inhibitor of the Wnt/β-catenin pathway, which causes the apoptosis of keratinocytes of the follicle and thus the entry into the catagen phase (latency) of the hair cycle;

P16, a cell cycle inhibitor, which is responsible for the premature senescence of fibroblasts of the dermal papilla.

In androgenetic alopecia, these three "signal" molecules are overexpressed. Indeed, dermal papilla fibroblasts from alopecic areas show an increase in P16 expression (Bahta A W et al. "Premature Senescence of Balding Dermal Papilla Cells In Vitro Is Associated with $P16^{INK4a}$ Expression" Journal of Investigative Dermatology, 128, 1088-1094 (2008)), of the secretion of IL-6 (Kwack M H & al. "Dihydrotestosterone-Inducible Dickkopf 1 from Balding's Dermal Papilla Cells Causes Apoptosis in Follicular Keratinocytes" Journal of Investigative Dermatology, 128, 262-269 (2008)) and the expression of DKK1 (Fawzi M M T & al. "Assessment of tissue levels of dickkopf-1 in androgenetic alopecia and alopecia areata." Journal of Cosmetic Dermatology, 15, 10-15 (2015)). These deregulations are also observed following treatment with DHT and may even be accentuated following the activation of the androgen signaling pathway (Yang et al. "Androgen Receptor Accelerates Premature Senescence of Human Dermal Papilla Cells in Association with DNA Damage". Plos One, 8, 1-10 (2013)).

Advantageously, the active ingredient of the invention is able to reduce the secretion of IL-6 and the expression of DKK1 and P16 in the fibroblasts of the dermal papilla. It thus makes it possible to correct the abnormal expression of the "signal" molecules involved in androgenetic alopecia.

In another aspect, epigenetics also plays a major role in the biology of hair. Epigenetics studies the mechanisms that can regulate the expression of genes in response to certain environmental stresses, without modifying the DNA pattern. All actors involved are grouped under the name of epigenome. Among them, miRNAs hold an important place. These small RNA molecules are able to inactivate genes on the basis of the environment by modifying the stability of their target messenger RNAs. It has recently been demonstrated that miRNAs regulate various processes such as proliferation and differentiation of dermal papilla fibroblasts and keratinocytes of the hair matrix. In addition, they regulate apoptosis during the catagen phase (Andl et al. "MicroRNAs (miRNAs) in the control of HF development and cycling: the next frontiers in hair research" Experimental dermatology, 24, 821-826 (2015)).

In an alopecic context, the fibroblasts of the dermal papilla have a deregulated miRNA expression profile. These modifications include overexpression of miR-3663-3p and of let-7a-3p (Lee et al. "Analysis of the microRNA expression of normal human dermal papilla cells treated with 5a-dihydrotestosterone" Molecular Medicine Reports, 12, 1205-1212 (2015)). Among the target genes for these miRNAs, some are involved in the Wnt/0-catenin signaling pathway, an essential pathway for hair growth. It is activated following the binding of a ligand of the Wnt family to its specific receptor and causes the accumulation of 0-catenin. Ultimately, this leads to proliferation of dermal papilla fibroblasts and induction of the hair growth phase (Ouji et al. "Maintenance of Dermal Papilla Cells by In Vitro Wnt-10b" Methods in Molecular Biology, 1516, 269-277 (2016)).

Advantageously, the active ingredient of the invention is able to limit the expression of miRNA 3663-3p and of let-7a-3p in fibroblasts of the dermal papilla. Thus, it attenuates epigenetic deregulations associated with androgenetic alopecia.

It is also known that the dermal papilla is the control center for hair growth. The fibroblasts of the papilla emit signals to the keratinocytes of the hair matrix in order to regulate the development of the hair. In a normal context, it takes place in a cycle having three phases:
  anagen: hair growth phase over 2 to 5 years;
  catagen: phase of degeneration lasting from a few days to a few weeks;
  telogen: latency phase for about 3 months.

In androgenetic alopecia, the alteration of the dynamics of the hair cycle is a major deregulation. It results in an increase in the proportion of hair in the telogen phase (latency), the duration of which is maintained or even lengthened. This is accompanied by a progressive shortening of the anagen phase (growth), marked by a decrease in expression of versican, a protein that is specific to this step (Soma et al. "Hair cycle-specific expression of versican in human hair follicles" Journal of Dermatological Science, 39, 147-154 (2005)). These deregulations as a whole are at the origin of the shrinking of hair follicles to such an extent that the hair no longer reaches the surface of the skin.

The active ingredient of the invention is able to stimulate the synthesis of versican in fibroblasts of the dermal papilla and thus preserve the activation of the dermal papilla. In addition, it improves the growth of hair follicles and helps to maintain a significant synthesis of versican and Ki-67. Thus, the active ingredient of the invention makes it possible to reduce the lack of growth associated with androgenetic alopecia by keeping hair follicles in the growth phase.

The invention thus relates to the use of an active ingredient of the invention by means of application to the hair and/or scalp, for fighting hair loss and activate its regrowth, especially in people with androgenetic alopecia. It acts on molecular abnormalities associated with androgenetic alopecia by correcting deregulation affecting the signal molecules and epigenetics and by stimulating mitochondrial dynamics. It is thus effective in normalizing two essential parameters for hair development, namely: activation of the dermal papilla and stimulation of the growth of hair follicles.

The active ingredient of the invention is preferably used in compositions, these compositions comprising a cosmetically acceptable medium. These are compositions in different galenic forms, suitable for application on the scalp and hair.

These compositions can, in particular, be in the form of oil-in-water emulsions, water-in-oil emulsions, multiple emulsions (Water/Oil/Water or Oil/Water/Oil), which can possibly be micro emulsions or nanoemulsions, or in the form of solutions, suspensions, hydrodispersions, aqueous gels or powders. They can be more or less fluid and have the appearance of lotion, shampoo, cream or mousse.

It may be compositions comprising at least 0.05% of a hydrolysate of *Pichia minuta* of the invention, preferably between 0.5 and 10%.

These compositions comprise, on top of the active ingredient, a physiologically acceptable and preferably cosmetically acceptable medium, i.e. which does not cause unacceptable discomfort for the user, such as redness, pulling or tingling.

The compositions of the invention may contain as adjuvant at least one compound chosen from:
  oils, which may be chosen in particular from silicone oils, whether linear or cyclic, volatile or non-volatile;
  waxes, such as ozokerite, polyethylene wax, beeswax or carnauba wax,
  silicone elastomers,
  surfactants, preferably emulsifiers, whether they are non-ionic, anionic, cationic or amphoteric,
  co-surfactants, such as linear fatty alcohols,
  thickeners and/or gelling agents,
  humectants, such as polyols like glycerin,
  dyes, preservatives, fillers,
  tensors,
  sequestering agents,
  perfumes,
  and their mixtures, without this list being limitative.

Examples of such adjuvants are specifically cited in the CTFA Dictionary (*International Cosmetic Ingredient Dictionary and Handbook* published by the *Personal Care Product Council*).

Of course, a person skilled in the art will carefully select any complementary compounds, whether active or non-active, and their quantity, so that the advantageous properties of the mixture are not, now or at a later stage, impaired by the planned addition.

These compositions are especially intended to be used for anti-hair loss and hair regrowth processes.

The invention thus also relates to a non-therapeutic method, namely a non-therapeutic cosmetic method for fighting hair loss and activating its regrowth, which includes applying a composition which includes an active ingredient of the invention to the hair and/or scalp, preferably at least once a day for at least one month. Preferably, the composition is a composition of the invention.

In order to illustrate these cosmetic effects for controlling hair loss and activation of the regrowth of hair, the following examples with their test results are presented.

EXAMPLES

Example 1: Active Ingredient of the Invention in Liquid Form

The active ingredient according to Example 1 is obtained by implementing the following steps:
- solubilization of the *Pichia minuta* biomass in water at 50 g/l,
- enzymatic hydrolysis with a proteolytic enzyme of bacterial origin,
- thermal inactivation, at 80° C., of the enzymatic activity,
- centrifugation decantation to recover the supernatant,
- filtration, and collection of the filtrate,
- sterilizing filtration on 0.22µ filter.

The hydrolysate obtained is in the form of a clear liquid, of a slightly orangish yellow color, with a weak odor.

It includes:
- 59% peptides by weight of dry matter, (determined by the LOWRY method),
- 15% sugars by weight of dry matter, (determined by the DUBOIS method),
- 26% ash by weight of dry matter, (determined by the weighing of the residues resulting from the incineration of the samples of the hydrolysate at 550° C. in an electric muffle furnace).

In addition, the peptides were characterized in order to determine their molecular weights and to quantify the various protein fractions by size exclusion FPLC chromatography.

The hydrolysate is analyzed under the following conditions:
- Pump: FPLC ÄKTA (Pharmacia)
- Column: Superdex Peptides TRICORN 10/300 GL (Pharmacia)
- Mobile phase: 20 mM potassium phosphate buffer, pH 7.2 with 0.25 M NaCl.
- Detector: UV at 280 nm
- Flow: 0.5 mL/min
- Injection volume: 200 µL A calibration curve of the retention time of the markers as a function of their molar mass is constructed (logarithmic fit). Table 1 summarizes the retention times obtained for the different markers.

TABLE 1

Retention time of the different markers.

| Molecules | Molecular weight (Da) | Retention time (min) |
| --- | --- | --- |
| Cytochrome C | 12,500 | 20.0 |
| Aprotinin | 6,512 | 23.5 |
| Vitamin B12 | 1,355 | 33.4 |
| Cytidine | 243 | 41.4 |

Thanks to the calibration curve, the following retention times could be estimated:
- protein of 10,000 Da: retention time=21.4 min
- protein of 3500 Da: retention time=25.2 min
- protein of 2000 Da: retention time=30.3 min Then, a fractionation program is constructed, on the basis of the retention times, in order to collect the following fractions (MM=molecular weight):

- fraction 1: 10,000 Da<MM
- fraction 2: 3,500 Da<MM<10,000 Da
- fraction 3: 2,000 Da<MM<3,500 Da
- fraction 4: 243 Da<MM<2,000 Da
- fraction 5: MM<243 Da The different fractions collected from the hydrolysate are quantified by spectrophotometric assay according to the LOWRY method (Lowry et al., Protein measurement with the folin reagent, J. Biol. Chem., 193, 265, 1951).

The chromatographic profile and the fractionation of the peptides of the hydrolysate are shown in FIG. 1 and the distribution of each fraction determined by spectrophotometric method is presented in Table 2.

TABLE 2

Distribution and Quantification of the Proteins of the Main Active Ingredient of Example 1

| Molecular weight (Da) | Division (%) |
| --- | --- |
| Fraction 1: 10,000 Da < MM | 0.3 |
| Fraction 2: 3,500 Da < MM < 10,000 Da | 2.9 |
| Fraction 3: 2,000 Da < MM < 3,500 Da | 10.5 |
| Fraction 4: 243 Da < MM < 2,000 Da | 83.3 |
| Fraction 5: MM < 243 Da | 3.0 |

More than 93% of peptides in the main active ingredient of Example 1 of the invention have molar masses of between 243 and 3500 Da. The amount of protein greater than 3500 Da represents less than 5% of the total protein.

An aminogram was also performed by HPLC chromatography of the hydrolysis of the product (concentrated hydrochloric acid for 24 hours) with detection with ninhydrin and the results are shown in Table 3 and in FIG. 2.

TABLE 3

Aminogram carried out on the hydrolysate of Example 1

| | g/100 g | Division |
| --- | --- | --- |
| Alanine | 2.32 | 9.6% |
| Arginine | 1.46 | 6.1% |
| Aspartic acid | 2.39 | 9.9% |
| Cystine | 0.19 | 0.8% |
| Glutamic acid | 4.99 | 20.9% |
| Glycine | 1.01 | 4.2% |
| Histidine | 0.40 | 1.7% |
| Isoleucine | 1.07 | 4.5% |
| Leucine | 1.99 | 8.3% |
| Lysine | 1.86 | 7.7% |
| Methionine | 0.29 | 1.2% |
| Phenylalanine | 0.66 | 2.7% |
| Proline | 0.75 | 3.1% |
| Serine | 1.33 | 5.5% |
| Threonine | 1.30 | 5.4% |
| Tyrosine | 0.60 | 2.5% |
| Valine | 1.45 | 6.0% |
| Total | 24.06 | 100.0% |

In addition, the ash distribution was determined after incineration at 550° C. The analysis of the minerals was carried out by optical emission spectrometry (ICP/OES) and the determination of chloride ions by titration with silver nitrate.

It is presented in Table 4 below:

TABLE 4

Ash distribution of the hydrolysate of Example 1

| | Ash distribution (%) |
|---|---|
| Calcium | 4 |
| Potassium | 18 |
| Magnesium | 1 |
| Sodium | 14 |
| Chlorine | 43 |
| Phosphorus | 12 |
| Sulfur | 7 |
| Not identified | 1 |

Example 2: Active Ingredient of the Invention in Solid Form (Hydrolysate of Example 1+Maltodextrin)

The active ingredient of Example 1 is combined with maltodextrin to constitute the active principle of Example 2.

It is obtained by implementing the following steps:
introduction of 50% of maltodextrin (mass) into the hydrolysate of Example 1,
concentration until reaching a concentration factor of 5,
debacterialization 5 min at 95° C.,
atomization.

The active ingredient is in the form of a powder having a particle size of less than 500 μm, a weak odor, a slightly orangish yellow color.

It includes (determination according to the same methods as for the hydrolysate in Example 1):
28% peptides by weight of dry matter,
58% sugars by weight of dry matter,
14% ash by weight of dry matter.

Since maltodextrin includes only non-active sugars, the peptide composition, the aminogram and the mineral composition of the active ingredient are identical to those of Example 1.

Example 3: Serum Regrows Hair

An exemplary composition of the invention in serum form includes:

| | | | |
|---|---|---|---|
| A. | Water | | qs 100% |
| | Preservative | | 0.7% |
| | Propylene glycol | | 30% |
| B. | Simulgel FL10 | (Seppic) | 0.5% |
| | DC200 | (Dow Corning) | 8% |
| C. | Lactic acid | | qs pH 5 |
| D. | Active ingredient | EXAMPLE 2: | 0.3% |

The pH of the composition is 5. It is in the form of an opalescent liquid, without odor.

The serum of Example 3 has the following characteristics: sprayable lotion, fresh and silky application, slippery effect, immediate penetration, soft and dry finish, smoothing effect on the hair.

It can be obtained by implementing the following steps:
Mix A and heat in a water bath at 50° C., making sure to disperse the preservative well,
Cool with stirring,
Add B, while stirring and adjust the pH with C,
Add D with stirring at 1,500 rpm and check the complete homogenization of the formula.

Example 4: Mask Regrows Hair

An example of a composition of the invention in the form of a mask for the hair, is constituted by:

| | | | |
|---|---|---|---|
| A. | Water | | qs 100% |
| | Preservative | | 0.7% |
| | Propylene glycol | | 20% |
| | Glucose acetate | | 6% |
| B. | Active ingredient | EXAMPLE 2: | 0.3% |
| C. | Simulquat HC305 | (Seppic) | 6% |

The pH of the composition is 4.5.
It is in the form of a thick and compact white gel.
The mask of Example 3 has the following characteristics: firm grip, easy application, film-forming effect, easy rinsing, soft and dry finish.

It can be obtained by implementing the following steps:
Mix A and heat in a water bath at 50° C., making sure to disperse the preservative well,
Add B with stirring and ensure good homogenization,
Add C with vigorous stirring (3,000 rpm) and stir until complete homogenization of the gel.

Example 5: Hair Regrowth Treatment

An example of a composition of the invention in the form of treatment for the hair, is constituted by:

| | | | |
|---|---|---|---|
| A. | Water | — | qs 100% |
| | Preservative | — | 0.7% |
| | Dub Diol | (Stéarinerie DUBOIS) | 20% |
| B. | Satiaxane CX930 | (Cargill) | 0.1% |
| | Satialgine US551 | (Cargill) | 3% |
| C. | Active ingredient | EXAMPLE 1: | 0.7% |
| D. | GENUGEL carrageenan CG-130 | (CP Kelco) | 2.5% |
| | Lauroyl Lysine | (HYTECH Laboratory) | 2% |
| | D-panthenol | (XINFU) | 1% |
| | Phytosqualane | (Sophim) | 1% |

The pH of the composition is 6.1.
It is in the form of a thick, smooth, odorless, unbleached gel.
The treatment of Example 5 has the following characteristics: Gentle grip, soft and even application on the skin and hair, cool and moisturizing effect, easy rinsing, smooth and soft finish.

It can be obtained by implementing the following steps:
Mix A and heat in a water bath at 50° C., making sure to disperse the preservative well,
Add B, stirring and ensure good homogenization of the gels,
Add C, and check the good dispersion of the active ingredient,
When cold, add D in the order indicated and stir (2,500 rpm) until complete homogenization.

Example 6: Treating Washing Base

An example of a composition of the invention in the form of treatment for the hair, is constituted by:

| | | | |
|---|---|---|---|
| A. | Oramix LS30 | (Seppic) | 25% |
| | Betadet S20 | (Kao Corporation) | 25% |
| | Oramix NS20 | (Seppic) | 20% |
| | Somepon T25 | (Seppic) | 4% |

-continued

| B. | Preservative | — | 1% |
|---|---|---|---|
|  | Carbopol Ultrez10 | (Novéon) | 0.1% |
| C. | ACTIVE INGREDIENT | EXAMPLE 1: | 0.7% |
| D. | NaOH | — | qs pH 4.8 |
| E. | Dub Grenn OD4 | (Stéarinerie DUBOIS) | 15% |
|  | Baobab Oil | (Sophim) | 5% |
|  | Biophytosebum | (Sophim) | 5% |

The pH of the composition is 5.

It is in the form of a liquid gelled base, slightly unbleached, odorless.

The washing base of Example 6 has the following characteristics: fluid flow, soft touch, extremely strong foaming power, good water dispersion with creation of a soft, white and compact foam, easy rinse, very slightly film-forming soft finish, moisturizing effect.

It can be obtained by implementing the following steps:

Mix A without stirring to avoid the formation of foam,

Add B, then C and stir gently, making sure that the powders are well dispersed.

Adjust the pH with D and with more intense stirring (1000 rpm), add the fatty phase and stir until the gel is completely homogenized.

Example 7: Treatment Lotion

An example of a composition of the invention in the form of a lotion for hair, includes:

| A. | Water | qs 100% |
|---|---|---|
|  | Preservative | 0.7% |
|  | Propylene glycol | 8% |
|  | Active ingredient EXAMPLE 2 | 0.3% |
| B. | Glycerol | 2.0% |
| C. | Alcohol | 10.0% |

It is in the form of an ethanolic lotion, transparent liquid.

It can be obtained by implementing the following steps:

Mix A without stirring to avoid the formation of foam,

Add B, then C, and stir gently, ensuring good dispersion.

EVALUATION OF THE COSMETIC EFFICACY OF THE INVENTION

I. In Vitro Tests

1 Effect of a Hydrolysate of *Pichia minuta* of the Invention on the Mitochondrial Dynamics Necessary for the Growth of Hair Follicles The objective of this study is to evaluate the effect of an active ingredient of the invention on the mitochondrial dynamics, an element necessary for the growth of hair follicles.

For this, the synthesis of mitofusin 1 was evaluated. Mitofusin 1 is a major player in mitochondrial fusion in human fibroblasts of the dermal papilla. When hair growth is encouraged, mitochondrial dynamics are modified. This results in an increase in the proportion of large fused mitochondria compared to small fissioned mitochondria in dermal papilla fibroblasts. This state is favorable for energy production.

The study was carried out by Western blot pursuant to the operating procedure described below.

On day 0, the human fibroblasts of the dermal papilla are inoculated into culture medium and incubated at 37° C.

On day 3, the cells are treated: the fibroblasts are treated with medium either containing or not the active ingredient at 0.02% and 0.04% (final V/V).

On day 5, the cell extracts are recovered and then stored at −80° C. waiting for assay by Western blot in accordance with the following characteristics:

electrophoresis is carried out on pre-cooled gel and the proteins are then transferred on a PVDF membrane, immunolabeling is carried out using a primary anti-mitofusin 1 antibody, the bands are visualized, semi-quantified by densitometry with a CCD camera, then analyzed using software.

The results are shown in Table 5.

TABLE 5

Effect of hydrolysate of *Pichia minuta* on mitofusin 1 synthesis by dermal papilla fibroblasts

|  | Mitofusin 1 level (UA) | Efficiency/Control (%) |
|---|---|---|
| Control | 0.929 |  |
| Active ingredient-Example 2 at 0.02% | 1.180 | 27 |
| Active Ingredient-Example 2 at 0.04% | 1.412 | 52 |

These results show that tested at 0.04%, a hydrolysate of *Pichia minuta* significantly increases mitofusin 1 synthesis by 52% in human fibroblasts of the dermal papilla. Thus, it acts favorably on the mitochondrial dynamics, a key element for the production of the energy necessary for the growth of hair follicles.

2. Effect of a Hydrolysate of *Pichia minuta* of the Invention on the Regulation of "Signal" Molecules Described in Androgenetic Alopecia The objective of this study is to evaluate the effect of an active ingredient of the invention on the regulation of "signal" molecules described in androgenetic alopecia.

For this, the study included evaluating dermal papilla fibroblasts treated with a solution of DHT mimicking alopecia:

IL-6 (interleukin 6), a cytokine secreted by human fibroblasts of the dermal papilla which inhibits hair growth;

DKK1 (Dickkopf 1), an inhibitor of the Wnt/β-catenin pathway, a major player in alopecia;

P16, a cell cycle protein associated with premature ageing of alopecia zone dermal papilla fibroblasts.

This study was carried out by ELISA and quantitative PCR, according to the operating protocol described below.

On day 0, the human fibroblasts of the dermal papilla are inoculated into culture medium and incubated at 37° C.

On day 3, the fibroblasts are treated with a solution of DHT containing or not the active ingredient at 0.02% and 0.04% (final V/V).

On day 5, at the end of the incubation, the cell supernatants are recovered. The IL-6 assay is performed using an ELISA assay kit. The RNAs were reverse-transcribed and the resulting complementary DNAs were analyzed by the quantitative PCR technique.

Expression of DKK1 and P16 mRNAs was also studied. In parallel, mRNAs of Ribosomal Protein S27 (RPS27), Hypoxanthine Phosphoribosyltransferase 1 (HPRT1), beta-Glucuronidase (GUSB) were analyzed as internal reference controls for standardization.

Quantification of fluorescence incorporation (SYBR Green) is continuously measured using a thermal cycler. The analysis of Ct (relative quantification) is performed using software.

The results are shown in Tables 6 and 7.

TABLE 6

Effect of a hydrolysate of *Pichia minuta* on the release of interleukin 6 by dermal papilla fibroblasts in a normal or alopecic model.

|  | IL-6 level (fg/µg of protein) | Ability to limit the secretion of IL-6 (%) |
|---|---|---|
| *Normal model* | | |
| Control | 1,284 | |
| Active ingredient-Example 2 0.04% | 1,182 | |
| *Alopecic model* | | |
| Control | 1,736 | |
| Active ingredient-Example 2 0.02% | 1,431 | 67 |
| Active ingredient-Example 2 0.04% | 1,299 | 97 |

TABLE 7

Effect of a hydrolysate of *Pichia minuta* on the expression of DKK1 and P16 by dermal papilla fibroblasts in a normal or alopecic model.

|  | DKK1 (%) | Ability to limit the expression of DKK1 (%) | P16 (%) | Ability to limit the expression of P16 (%) |
|---|---|---|---|---|
| *Normal model* | | | | |
| Control | 100 | | 100 | |
| Active ingredient-Example 2 0.04% | 92 | | 105 | |
| *Alopecic model* | | | | |
| Control | 212 | | 195 | |
| Active ingredient-Example 2 0.02% | 132 | 71 | 139 | 59 |
| Active ingredient-Example 2 0.04% | 110 | 91 | 128 | 71 |

It is found that DHT significantly increases IL-6 secretion and expression of DKK1 and P16 by human fibroblasts of the dermal papilla, thus mimicking the expression modification of "signal" molecules described in androgenetic alopecia.

Tested at 0.04%, the active ingredient of the invention makes it possible to significantly limit the secretion of IL-6 by 97% and the expressions of DKK1 and P16 by 91% and 71%, respectively.

Thus, it corrects the abnormal production of "signal" molecules involved in androgenetic alopecia.

3. Effect of a Hydrolysate of *Pichia minuta* of the Invention on the Epigenetic Modifications Associated with Androgenetic Alopecia The objective of this study is to evaluate the effect of an active ingredient of the invention on the epigenetic modifications associated with androgenetic alopecia.

For this, the expression of miRNA in a model of human dermal papilla fibroblasts, treated with a solution of dihydrotestosterone (DHT) (in order to mimic alopecia) was evaluated. This study focuses on two miRNAs involved in hair growth: 3663-3p and let-7a-3p whose expressions are induced by DHT. Among the biological pathways targeted by these miRNAs is the Wnt/βcatenin signaling pathway which is essential for hair growth.

The study was carried out by quantitative PCR, according to the following operation protocol.

On day 0, the human fibroblasts of the dermal papilla are inoculated in culture medium and incubated at 37° C. in an atmosphere containing 5% $CO_2$.

On day 3, the fibroblasts are treated with a solution of DHT which does or does not contain the active ingredient of the invention at 0.02% and 0.04% (final V/V).

On day 4, the RNAs were reverse-transcribed and the resulting complementary DNAs were analyzed by quantitative PCR technique.

The expression of microRNAs: 3663-3p and let-7a-3p has been studied.

In parallel, small nucleolar RNA C/D box 68 (SNORD68) was analyzed as an internal reference control for standardization, Quantification of fluorescence incorporation is measured continuously using a thermocycler. The analysis of the Ct (relative quantification) is performed using software.

The results are shown in Table 8.

TABLE 8

Effect of a hydrolysate of *Pichia minuta* on the expression of 3663-3p and let-7a-3p miRNAs by dermal papilla fibroblasts in a normal or alopecia model.

|  | miRNA 3663-3p (%) | Ability to limit the expression of miRNA 3663-3p (%) | miRNA let-7a-3p (%) | Ability to limit the expression of miRNA let-7a-3p (%) |
|---|---|---|---|---|
| *Normal model* | | | | |
| Control | 100 | | 100 | |
| Active ingredient-Example 2 0.04% | 86 | | 120 | |
| *Alopecic model* | | | | |
| Control | 172 | | 172 | |
| Active ingredient-Example 2 0.02% | 143 | 40 | 125 | 65 |
| Active ingredient-Example 2 0.04% | 136 | 50 | 108 | 89 |
| Active ingredient-Example 1 0.04% | 133 | 54 | | |

DHT induces expression of 3663-3p and let-7a-3p miRNAs in human dermal papilla fibroblasts, mimicking the epigenetic changes associated with androgenetic alopecia.

It is found that, tested at 0.04%, a hydrolysate of *Pichia minuta* significantly reduces the expression of miRNA 3663-3p and let-7a-3p by respectively 50% and 89%.

Thus, an active ingredient of the invention makes it possible to limit the epigenetic modifications associated with androgenetic alopecia.

4. Effect of a Hydrolysate of *Pichia minuta* of the Invention on the Activity of the Dermal Papilla in Androgenetic Alopecia The objective of this study is to evaluate the effect of an active ingredient of the invention on the activation of the dermal papilla.

For this, the versican synthesis was measured. It is a proteoglycan that is specific to the growth phase. The evaluation was performed in a 3D model of fibroblasts in the form of spheroids, treated with a solution of DHT. This model mimics the inactivation of the dermal papilla, a factor contributing to the lack of growth associated with androgenetic alopecia.

The study was performed by immunohistological staining according to the following operating protocol.

On day 0, the human fibroblasts of the dermal papilla are inoculated into culture medium and incubated at 37° C.

On day 1, the spheroids formed are treated with a solution of DHT which does or does not contain the active ingredient of the invention at 0.04% (final V/V).

On day 4, the spheroids are recovered and secured.

Immunohistological labeling of versican is performed. Visualization is performed on a confocal microscope coupled to an image analysis system.

Versican synthesis is proportional to the intensity of fluorescence (green color) present on the spheroids.

The nuclei of the cells appear to be blue in color.

The results being qualitative, we defined 3 levels of synthesis of versican:
Low synthesis +
Average synthesis ++
Strong synthesis +++
The results are given in Table 9.

TABLE 9

Effect of a hydrolysate of *Pichia minuta* on the synthesis of versican in dermal papilla fibroblasts spheroids in an alopecic model.

| | Synthesis of versican |
|---|---|
| Normal model | |
| Control | +++ |
| Alopecic model | |
| Control | + |
| Active principle-example 2 0.04% | ++ |

DHT induces a decrease in the synthesis of versican, in a model of human fibroblasts of dermal papilla in the form of spheroids, mimicking an inactivation of the dermal papilla induced during androgenetic alopecia.

It is found that when tested at 0.04%, the active ingredient of the invention stimulates the synthesis of versican in this model. Thus, it helps maintain the activity of the dermal papilla and its ability to induce the growth of hair follicles.

5. Effect of a Hydrolysate of *Pichia minuta* of the Invention on the Growth of Hair Follicles in Androgenetic Alopecia The objective of this study is to evaluate the ability of an active ingredient of the invention to maintain hair follicles in a growth phase (anagen phase).

For this, we conducted a study on the ex vivo hair follicle culture model developed by Philpott et al. treated with a solution of DHT in order to mimic the growth reduction associated with androgenetic alopecia. This ability was evaluated by measuring:
the elongation of hair follicles;
the synthesis of versican and Ki-67, two key proteins of hair growth.

The evaluation of the elongation is carried out by measuring the size of hair follicles after photographs. The syntheses of versican and Ki-67 are studied by immunohistological labeling. The operating protocol is described hereafter.

On day 0, the hair follicles are obtained from scalp fragments and incubated in culture medium at 37° C.

On day 1, the follicles are photographed and measured on a microscope coupled to an image analysis system.

The follicles selected (in the anagen phase) are then treated with a solution of DHT which does or does not contain the active ingredient of the invention at 0.02% and 0.04% (final V/V).

On day 5, two studies are carried out: the study of the elongation of hair follicles and the study of synthesis of Versican and Ki-67.

Study of the elongation of hair follicles

The follicles are photographed and measured on a microscope coupled to an image analysis system. The elongation of each follicle is equal to its growth between day 0 and day 5.

The follicles are treated with a solution of DHT containing or not the active ingredient at 0.02% and 0.04% (final V/V).

Study of the synthesis of versican and Ki-67

The follicles are recovered and included in Tissue-Tek® and then frozen. Sections (4 μm) are then made using a cryostat. Immunohistological labeling of versican and Ki-67 is performed. Visualization is performed on a confocal microscope coupled to an image analysis system.

Versican synthesis is proportional to the intensity of fluorescence (green color) present on sections of hair follicles.

The synthesis of Ki67 is proportional to the intensity of the fluorescence (yellow color) present on sections of hair follicles.

On day 7, the follicles are again photographed and measured. The elongation of each follicle is equal to its growth between day 0 and day 7.

The results of the effect on the elongation of hair follicles are given in Table 10.

TABLE 10

Effect of a hydrolysate of *Pichia minuta* on the growth of hair follicles ex vivo in an alopecic model.

| | Elongation (μm) | Ability to restore elongation (%) |
|---|---|---|
| Day 0-day 5 | | |
| Normal model | | |
| Control | 1,201 | |
| Alopecic model | | |
| Control | 743 | |
| Active principle-Example 2 0.02% | 822 | +11 |
| Active ingredient-Example 2 0.04% | 887 | +31 |
| Day 0-day 7 | | |
| Normal model | | |
| Control | 1,617 | |
| Alopecic model | | |
| Control | 961 | |
| Active principle-Example 2 0.02% | 1,038 | +12 |
| Active ingredient-Example 2 0.04% | 1,206 | +37 |

It is found that DHT significantly reduces the growth of hair follicles at day 5 and day 7 by −31% and −37%, respectively. As a result, DHT mimics the lack of hair growth associated with androgenetic alopecia.

Tested at 0.04%, an active ingredient of the invention makes it possible to significantly increase the growth of hair follicles on day 5 and day 7 by respectively +31% and +37%.

The results of the effect on hair matrix of hair follicles are given in Table 11.

The results being qualitative, 3 synthesis levels of versican and Ki-67 were defined:

TABLE 11

Effect of a hydrolysate of *Pichia minuta* on the synthesis of versican and Ki-67 by ex vivo hair follicles in an alopecic model.

| | Synthesis of Versican and Ki-67 |
|---|---|
| Normal model | |
| Control | +++ |
| Alopecic model | |
| Control | + |
| Active ingredient-Example 2 0.04% | ++ |

Low synthesis +
Average synthesis ++
Strong synthesis +++

It is found that DHT significantly reduces the synthesis of versican and Ki-67. As a result, DHT mimics the metabolic alterations associated with androgenetic alopecia.

Tested at 0.04%, an active ingredient of the invention makes it possible to maintain a significant synthesis of versicans, and the proliferative power of keratinocytes.

Thus, the use of the invention makes it possible to limit the reduction in growth associated with androgenetic alopecia and keeps hair follicles in an anagen phase.

II. In Vivo Tests

The volunteers participating in the in vivo tests were selected according to several criteria. These are men under 55 years of age, with mild to moderate alopecia and a minimum of 20% hair in the telogen phase.

1 Effect of a Hydrolysate of *Pichia minuta* of the Invention on Capillary Growth The objective of this study was to evaluate, in vivo, the anti-hair loss effect of an active ingredient of the invention (Example 2) formulated at 0.3% in a lotion (Example 7), in volunteers with mild to moderate alopecia.

This study was conducted on 22 volunteers aged between 31 and 55 (mean age 43±8 years), having applied 1 ml of the lotion of the invention every morning and evening for 8 months.

The anti-hair loss effect was studied by the phototrichogram method from measurements taken at time 0, 3, 6 and 8 months after the start of treatment. The following parameters were analyzed:
capillary density,
quantity of hair in the anagen phase: indicator of hair growth;
quantity of hair in telogen phase: indicator of hair loss;
Anagen/Telogen ratio: hair growth coefficient.

A summary of results on capillary density is presented in Table 12.

TABLE 12

Effect of a hydrolysate of *Pichia minuta* formulated at 0.3% of capillary density after 3, 6 and 8 months of twice-daily application.

| | Variation/day 0 (%) |
|---|---|
| 3 months | +21.3 |
| 6 months | +22.1 |
| 8 months | +24.9 |

It is found that an active ingredient of the invention, formulated at 0.3% increases the capillary density already after 3 months of application (+21.3%). This effect is prolonged and intensified after 6 and 8 months of treatment (respectively +22.1 and +24.9%).

A summary of results on hair growth is presented in Table 13.

TABLE 13

Effect of a hydrolysate of *Pichia minuta* formulated at 0.3% of hair growth after 3, 6 and 8 months of twice-daily application.

| | Variation/Day one (%) | |
|---|---|---|
| | Hair in growth phase (anagen phase) (%) | Improvement of the Anagen/Telogen ratio (%) |
| 3 months | +24.7 | +73.1 |
| 6 months | +38.7 | +85.7 |
| 8 months | +49.1 | +112.7 |

It is found that the active ingredient of the invention shows an action on capillary growth, already after 3 months of application, which intensifies during treatment.

This results in a statistically significant increase in the proportion of hair in the anagen phase. In addition, there is a significant increase in the Anagen/Telogen ratio.

A summary of the results on the reduction of the quantity of hair in capillary telogen phase is presented in Table 14.

This parameter, characteristic of a reduction in hair loss, was evaluated by phototrichogram.

TABLE 14

Effect of a hydrolysate of *Pichia minuta* formulated at 0.3% of hair loss in the telogen phase after 3, 6 and 8 months of twice-daily application.

| | Variation/Day one (%) |
|---|---|
| 3 months | −14.0 |
| 6 months | −21.9 |
| 8 months | −26.1 |

Under the conditions of this study, the active ingredient of the invention formulated at 0.3% in a lotion significantly reduces the proportion of hair in the telogen phase after 3 months of application (−14.0%). This effect intensifies after 6 and 8 months of treatment (respectively −21.9% and −26.1%).

These different results are illustrated in FIGS. 5A/6A (at day 0 before application) and 5B/6B (after 8 months of application). The total hair gain on the scalp between day 0 and 8 months for this illustration is 74,160 hairs.

By stimulating hair growth (anagen phase) and decreasing the proportion of hair in the telogen phase, the use of an active ingredient of the invention makes it possible to strengthen and redensify the hair.

2. Effect of a Hydrolysate of *Pichia minuta* of the Invention on Hair Loss

The objective of this study was to evaluate, in vivo, the ability of an active ingredient of the invention (Example 2) formulated at 0.3% in a lotion (Example 7), to curb the hair loss of volunteers with mild to moderate alopecia.

This study was performed on 22 volunteers aged between 31 and 55 (mean age 43±8 years), having applied 1 ml of the lotion of the invention every morning and evening.

The magnitude of hair loss was studied using the wash test method performed before starting and 3, 6 and 8 months after the start of treatment.

A summary of the results corresponding to the effect of an active principle of the invention formulated at 0.3% on the hair loss evaluated by means of counting after wash testing is presented in Table 15.

TABLE 15

Effect of a hydrolysate of *Pichia minuta* formulated at 0.3% in a lotion on hair loss after 3, 6 and 8 months of twice-daily application.

|  | Variation/Day one (%) |
|---|---|
| 3 months | −21.2% |
| 6 months | −30.9% |
| 8 months | −34.0% |

Under the conditions of this study, already after 3 months of twice-daily applications, the composition of the invention slows hair loss by reducing the number of hairs recovered after shampooing by 21.2%.

This effect is prolonged and intensified after 6 months of treatment to achieve an average decrease in hair loss of 30.9%, the maximum decrease being 81%. More than 8 out of 10 volunteers presented this effect.

Finally, after 8 months of treatment, the invention stabilizes hair loss by limiting the number of hairs lost by 34.0%.

COMPARATIVE TESTS: COMPARISON OF THE ACTIVE PRINCIPLE OF THE INVENTION WITH OTHER HYDROLYSATES OF YEAST

Comparative Test 1

The purpose of this test is to show the importance of the choice of yeast.

An identical enzymatic hydrolysis process was implemented on 3 biomasses:
a *Pichia minuta* biomass
a *Pichia heedii* biomass
a *Saccharomyces cerevisiae* biomass This method included the implementation of the following steps:
solubilization of biomass in water at 100 g/L,
enzymatic hydrolysis using a protease,
enzymatic inactivation thermally at 80° C. for 1 hour,
decantation to remove the insoluble phase, recover supernatant,
filtration, and recovery of the filtrate.

The analytical characteristics of the products obtained are presented in the table below:

TABLE 16

Analytical characteristics of the three hydrolysates of yeast

|  | Hydrolysate of *Pichia minuta* | Hydrolysate of *Pichia heedii* | Hydrolysate of *Saccharomyce cerevisiae* |
|---|---|---|---|
| Dry matter (MS) g/L | 36 | 22 | 24 |
| pH | 5.4 | 5.5 | 5.2 |
| Color L, a, b | 99.48 | 99.42 | 99.97 |
|  | −0.78 | −1.18 | −0.27 |
|  | 3.29 | 3.95 | 0.78 |
| Ash g/L | 7.8 | 4.6 | 4.1 |
| % ash/MS | 21.7% | 20.9% | 17.1% |
| Protein (Lowry method) g/L | 18.6 | 6.8 | 1.5 |
| % Protein/MS | 52% | 31% | 6% |

It can be seen that these hydrolysates do not have the same analytical characteristics, especially as regards the protein content, which are very different for the three products obtained from the same process, but from different yeasts.

The size of the proteins is also different, as can be seen in the chromatogram of the proteins of the three products, as shown in FIG. 3.

These 3 hydrolysates were then tested for their effect on the expression of P16, the tests having been carried out according to the conditions and the protocol described in point 1.2 of the evaluation part of the cosmetic effect of the present application.

The results obtained are shown in Table 17.

TABLE 17

Ability of the three hydrolysates to inhibit P16.

|  | P16 (%) | Ability to limit the expression of P16 (%) |
|---|---|---|
| Normal model | | |
| Control | 100 | |
| Alopecic model | | |
| Control | 195 | |
| Hydrolysate of *Pichia minuta* 0.04% | 128 | 71 |
| Hydrolysate of *Pichia heedii* 1% | 222 | 0 |
| Hydrolysate of *Saccharomyces cerevisiae* 1% | 214 | 0 |

These results clearly show that the choice of yeast is important, since a same production process of the active ingredient applied to 3 yeast biomasses of the same family, leads to three different products, only one of which is effective on a key parameter in fighting hair loss.

Comparative Test 2

The aim of this test is to compare the effectiveness of a cosmetic active ingredient, a hydrolysate of *Pichia anomala* described in patent FR3016521, with that of the active ingredient of the invention in order to show that a cosmetic active ingredient derived from a yeast of the genus *Pichia*, does not necessarily work.

The analytical characterization of the two active ingredients is presented in Table 18.

TABLE 18

Analytical characteristics of both hydrolysates

|  | Hydrolysate of Pichia minuta | Hydrolysate of Pichia anomala (FR3016521) |
|---|---|---|
| % Ash/MS | 26% | 34.7% |
| % Protein/MS | 59% | 59% |
| % sugars/MS | 15% | 6.3% |

It is found that these hydrolysates have similar analytical characteristics, especially with regard to the protein contents which are identical.

The characterization of the protein fraction is presented in Table 19.

TABLE 19

Characterization of the protein fraction of the two hydrolysates

| Hydrolysate of Pichia anomala (FR3016521) | | Hydrolysate of Pichia minuta | |
|---|---|---|---|
| Fraction 1: Mm > 5000 Da | 13.0% | Fraction 1: Mm > 10,000 Da | 0.3% |
| Fraction 2: 2000 < Mm ≤ 5000 Da | 38.4% | Fraction 2: 3500 < Mm ≤ 10 000 Da | 2.9% |
|  |  | Fraction 3: 2000 < Mm ≤ 3500 Da | 10.5% |
| Fraction 3: 243 < Mm ≤ 2000 Da | 46.3% | Fraction 4: 243 < Mm ≤ 2000 Da | 83.3% |
| Fraction 4: 0 < Mm ≤ 243 Da | 2.3% | Fraction 5: 0 < Mm ≤ 243 Da | 3.0% |

Protein size is also similar, since both hydrolysates contain 59% protein, more than 87% of which have a molecular weight of less than 5 kDa.

These 2 hydrolysates were then tested for their effect on the expression of P16, the tests having been carried out according to the conditions and the protocol described in point 1.2 of the evaluation part of the cosmetic effect of the present application.

The results obtained are shown in Table 20.

TABLE 20

Ability of both hydrolysates to inhibit P16.

|  | P16 (%) | Ability to limit the expression of P16 (%) |
|---|---|---|
| Normal model | | |
| Control | 100 | |
| Alopecic model | | |
| Control | 195 | |
| Hydrolysate of Pichia minuta 0.04% | 128 | 71 |
| Hydrolysate of Pichia anomala 1% | 225 | 0 |

These results still show that it is obvious that the choice of yeast is important, since a hydrolysate of Pichia anomala from a yeast of the Pichia genus, also having the same protein content as the hydrolysate of Pichia minuta to which it is compared, does not show efficacy on the chosen capillary marker.

Comparative Test 3

The aim of this test is to compare the effectiveness of a hydrolysate of Torulaspora delbrueckii, described in patent FR2979541, with that of the active ingredient of the invention of Example 1, in order to show that a cosmetic active ingredient derived from a yeast having a similar analytical characteristic, does not necessarily work.

The analytical characterization of the two active ingredients is presented in Table 21.

TABLE 21

Analytical characteristics of both hydrolysates

|  | Hydrolysate of Pichia minuta | Hydrolysate of Torulaspora delbrueckii (FR2979541) |
|---|---|---|
| % ash/MS | 26% | 28.3% |
| % Protein/MS | 59% | 64.3% |
| % sugars/MS | 15% | 6.95% |
| % Polyphenols/MS | 0% | 0.25% |

It is found that these hydrolysates have similar analytical characteristics, particularly with regard to the protein contents which are close.

The characterization of the protein fraction is presented in Table 22.

TABLE 22

Characterization of the protein fraction of the two hydrolysates

| Hydrolysate of<br>Torulaspora delbrueckii<br>(FR2979541) | | Hydrolysate of<br>Pichia minuta | |
|---|---|---|---|
| Fraction 1:<br>Mm > 5000 Da | 3.3% | Fraction 1:<br>Mm > 10,000 Da | 0.3% |
| Fraction 2:<br>2000 < Mm ≤ 5000 Da | 25.64% | Fraction 2:<br>3500 < Mm ≤ 10 000 Da | 2.9% |
| | | Fraction 3:<br>2000 < Mm ≤ 3500 Da | 10.5% |
| Fraction 3:<br>243 < Mm ≤ 2000 Da | 68.29% | Fraction 4:<br>243 < Mm ≤ 2000 Da | 83.3% |
| Fraction 4:<br>0 < Mm ≤ 243 Da | 2.77% | Fraction 5:<br>0 < Mm ≤ 243 Da | 3.0% |

Protein size is also similar, since both hydrolysates contain more than 93% having a molecular weight of less than 5 kDa.

These 2 hydrolysates were then tested for their effect on the expression of P16, the tests having been carried out according to the conditions and the protocol described in point 1.2 of the evaluation part of the cosmetic effect of the present application.

The results obtained are shown in Table 23.

TABLE 23

Ability of both hydrolysates to inhibit P16.

| | P16 (%) | Ability to limit the expression of P16 (%) |
|---|---|---|
| Normal model | | |
| Control | 100 | |
| Alopecic model | | |
| Control | 195 | |
| Hydrolysate of<br>Pichia minuta 0.04% | 128 | 71 |
| Hydrolysate of<br>Torulaspora delbrueckii 1% | 201 | 0 |

These results further show that the choice of yeast is important, since a hydrolysate of another yeast having a similar analytical characterization (protein/ash/sugar content) and identical protein sizes (93% of proteins<5000 Da), has no efficacy on the chosen capillary marker.

Comparative Test 4

The objective of this test is to demonstrate that a hydrolysate of Pichia minuta does not have the same analytical characteristics and is therefore different from a Pichia minuta biomass, as it exists in nature.

First, the hydrolysate does not contain live yeasts whereas the biomass contains them.

The method of microorganism culture on agar, allows this verification. It has been used for the hydrolysate of Example 1 on the one hand and for a biomass of Pichia minuta on the other hand:

Isolation by dial streak at the angle of 1 μL,
Culture medium: Sabouraud
Incubation 48 h at 30° C.

The results are shown in FIG. 4B for the hydrolysate and in FIG. 4A for the biomass.

No growth is not observed (FIG. 4B) on the agar with the hydrolysate of example 1, whereas on the other hand (FIG. 4A) a growth of white, round, shiny, oily colonies with a diameter of less than 0.5 mm is observed on agar with Pichia minuta biomass.

The analytical characterization of the hydrolysate of Example 1 and a biomass of Pichia minuta is further presented in Table 24.

TABLE 24

Analytical characteristics of the hydrolysate of the invention and of a biomass of Pichia minuta

| | Hydrolysate of<br>Pichia minuta<br>(Example 1) | Biomass of<br>Pichia minuta |
|---|---|---|
| % ash/MS | 26% | 8% |
| % Protein/MS | 59% | 41% |
| % sugars/MS | 15% | 36% |
| Not determined | — | 15% |

These results show that there are important analytical differences between biomass and hydrolysate of Pichia minuta. Biomass is the natural raw material on which the enzymatic hydrolysis process is applied to obtain the active ingredient of the invention, hydrolysate of Pichia minuta.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A method for fighting hair loss and activating hair regrowth, the method comprising:
    applying an active ingredient comprising a hydrolysate of Pichia minuta to a hair, or a scalp, or both of an individual to reduce hair loss, or activate hair regrowth, or both.

2. The method of claim 1, wherein the hydrolysate of Pichia minuta comprises peptides.

3. The method of claim 2, wherein at least 50% by weight of the peptides of the hydrolysate are peptides having a molecular weight of less than 3500 Da.

4. The method of claim 2, wherein the peptides comprise peptides with a molecular weight of less than 3500 Da and the peptides with a molecular weight of less than 3500 Da represent at least 40% of a weight of a total dry material of the hydrolysate.

5. The method of claim 1, wherein the hydrolysate comprises at least 5% of peptides by weight of a dry matter of the hydrolysate.

6. The method of claim 1, wherein the hydrolysate further comprises at least one mineral.

7. The method of claim 1, wherein the cosmetic active ingredient is a liquid.

8. The method of claim 1, wherein the hydrolysate is an enzymatic or chemical hydrolysate.

9. The method of claim 1, wherein the active ingredient is a solid and further comprising an atomization carrier selected from the group consisting of: maltodextrin, gum arabic, soy lecithin, and isomalt.

10. The method of claim 9, wherein the hydrolysate of *Pichia minuta* represents between 25 and 75% of the weight of the active ingredient.

11. The method of claim 1, wherein the individual has androgenetic alopecia.

12. The method of claim 1, wherein the method is for activating the dermal papilla and stimulating the growth of hair follicles.

13. The method of claim 1, wherein the active ingredient is formulated as a composition comprising at least 0.05% by weight of the active ingredient in liquid form.

14. The method of claim 13, wherein the composition is in the form of a lotion, shampoo, cream, or mousse.

15. The method of claim 1, wherein the active ingredient is applied to the hair or the scalp of the individual at least once a day for at least one month.

* * * * *